United States Patent [19]

Behre et al.

[11] Patent Number: 4,609,503

[45] Date of Patent: Sep. 2, 1986

[54] PROCESS FOR THE PREPARATION OF 1-AMINO-8-NAPHTHOL-4,6-DISULPHONIC ACID (K-ACID)

[75] Inventors: Horst Behre; Heinz U. Blank, both of Odenthal; Willi Schössler, Cologne, all of Fed. Rep. of Germany

[73] Assignee: Bayer Aktiengesellschaft, Leverkusen, Fed. Rep. of Germany

[21] Appl. No.: 195,024

[22] Filed: Oct. 8, 1980

Related U.S. Application Data

[63] Continuation of Ser. No. 76,052, Sep. 17, 1979, abandoned.

[30] Foreign Application Priority Data

Oct. 6, 1978 [DE]  Fed. Rep. of Germany ....... 2843680

[51] Int. Cl.$^4$ ............................................ C07C 143/64
[52] U.S. Cl. .................................................. 260/509
[58] Field of Search ......................................... 260/509

[56] References Cited

U.S. PATENT DOCUMENTS 4,111,979  9/1978  Kotera et al. ...................... 260/509
4,166,826  9/1979  Schössler et al. .................. 260/509

Primary Examiner—Alan Siegel
Attorney, Agent, or Firm—Sprung Horn Kramer & Woods

[57] ABSTRACT

The invention relates to a process for the preparation of 1-amino-8-naphthol-4,6-disulphonic acid (K-acid) as the mono-alkali metal salt by reacting a mixture of naphthylaminetrisulphonic acids and/or salts thereof with an alkali metal salt solution and separating the K-acid as the mono-alkali metal salt, by acidification and crystallization. The product is a known valuable dyestuff intermediate.

2 Claims, No Drawings

PROCESS FOR THE PREPARATION OF 1-AMINO-8-NAPHTHOL-4,6-DISULPHONIC ACID (K-ACID)

This is a continuation of Application Ser. No. 76,052, filed Sept. 17, 1979, now abandoned.

The present invention relates to a process for the preparation of 1-amino-8-naphthol-4,6-disulphonic acid (K-acid) as a mono-alkali metal salt from naphthylamine-trisulphonic acid isomer mixtures by alkaline hydrolysis under pressure.

1-Amino-8-naphthol-4,6-disulphonic acid, which is frequently also called K-acid, is an important intermediate product in the preparation of dyestuffs (see Ullmann's Enzyklopädie der technischen Chemie (Ullmann's Encyclopaedia of Industrial Chemistry), 3rd Edition, Volume 12, page 622).

It is known from FIAT Final Report No. 1016, pages 42–44 and BIOS Final Report No. 1152 (item No. 22, page 105) that K-acid can be prepared as follows:

Naphthalene is introduced into sulphuric acid monohydrate (100% pure $H_2SO_4$) at 30° to 35° C. whilst simultaneously running in 65% strength oleum, and the reaction mixture is kept at 50° C. for one hour, at 70° C. for one hour and at 90° C. for seven hours. The resulting naphthalenetrisulphonic acid isomer mixture is nitrated with mixed acid. After diluting the mixture with water, expelling the nitrous gases and separating off the sulphuric acid as calcium sulphate, the isomer mixture of nitronaphthalenetrisulphonic acids is reduced with iron and dissolved iron salts are then precipitated with magnesium oxide and separated off. The acid calcium salt of T-acid (1-naphthylamine-3,6,8-trisulphonic acid) is first precipitated by adding hydrochloric acid and is filtered off and washed with brine. Crude 1-naphthylamine-4,6,8-trisulphonic acid (naphthamine triacid K, melanic acid) is then separated out of the filtrate as the acid disodium salt by adding sodium chloride and hydrochloric acid and is washed with salt water. For purification, the crude product is suspended in water and dissolved with sodium carbonate, the solution is filtered to remove calcium carbonate and concentrated and the pure melanic acid is prepcipitated as the acid disodium salt by adding hydrochloric acid and is filtered off.

The acid disodium salt of melanic acid is reacted with sodium hydroxide and water under pressure at 170° C. in the course of 12 hours. K-Acid is then obtained as the acid monosodium salt by adding hydrochloric acid and water, followed by filtration.

The disadvantage of this process is that T-acid must first be separated off as the acid calcium salt and melanic acid must then be separated off as the acid disodium salt in an intermediate stage, and the latter must be purified by redissolving and crystallising. An effluent which is extremely difficult and expensive to work up since it contains, in addition to organic constituents, large amounts of sodium chloride, calcium chloride and hydrochloric acid is obtained in this procedure.

The acid calcium salt of T-acid separated out must furthermore be converted into the trisodium salt by a sodium carbonate treatment if, for example, it is to be converted into 1-amino-8-naphthol-3,6-disulphonic acid (H-acid) according to FIAT Final Report No. 1016, pages 33–36.

Melanic acid is not completely separated out as the acid disodium salt, and redissolving and crystallising the crude product leads to further losses in yield. The moist melanic acid salt separated out still contains sodium chloride and adhering hydrochloric acid. These can only be washed out with loss of melanic acid. If the two components are left in the melanic acid, subsequent reaction with sodium hydroxide and water requires an increased consumption of sodium hydroxide in order to establish the necessary concentration of caustic alkali in the reaction mixture.

On acidifying the alkaline reaction solution with hydrochloric acid, considerable amounts of 1-amino-6-naphthol-4,8-disulphonic acid (iso-K-acid) are separated out together with K-acid, as a repeat experiment has shown (compare Example 5).

This by-product can be removed only by expensive purification operations. Furthermore, an effluent which is extremely difficult and expensive to work up since it contains, in addition to the organic constituents, large amounts of sodium chloride and hydrochloric acid is also obtained at this point.

A process for the preparation of mono-alkali metal salts of 1-amino-8-naphthol-4,6-disulphonic acid has now been found, which is characterised in that a mixture of naphthylaminetrisulphonic acids and/or salts thereof is reacted with an alkali metal hydroxide solution under increased pressure and at elevated temperature and 1-amino-8-naphthol-3,6-disulphonic acid (H-acid) and 1-amino-8-naphthol-4,6-disulphonic acid (K-acid) are then isolated, in each case in the form of their mono-alkali metal salts, by acidification and crystallisation.

Examples of suitable feed products are naphthylaminetrisulphonic acid isomer mixtures which are obtained during the industrial preparation of naphthamine triacid K (melanic acid). Mixtures which can be employed in the process according to the invention generally contain over 40% by weight of 1-naphthylamine-4,6,8-trisulphonic acid (melanic acid), relative to the total amount of diazotisable substances calculated with a molecular weight of 383. Those mixtures which contain 45 to 65% by weight of 1-naphthylamine-4,6,8-trisulphonic acid are preferably employed. A naphthylaminetrisulphonic acid mixture which is particularly preferably to be employed contains 50 to 60% by weight of 1-naphthylamine-4,6,8-trisulphonic acid, 25 to 35% by weight of 1-naphthylamine-3,6,8-trisulphonic acid, 5 to 10% by weight of 2-naphthylamine-4,6,8-trisulphonic acid, 0.5 to 2% by weight of 1-naphthylamine-2,5,7-trisulphonic acid, 0.1 to 2% by weight of 1-naphthylamine-3,5,7-trisulphonic acid and 0.1 to 0.5% by weight of 2-naphthylamine-3,6,8-trisulphonic acid.

Such mixtures can be obtained, for example, by trisulphonating naphthalene, nitrating the mixture formed and then reducing the nitronaphthalenetrisulphonic acid mixture present. These reactions can be carried out by the procedure described initially, according to FIAT Final Report No. 1016, pages 42 to 44, or in any other manner.

The naphthylaminetrisulphonic acid mixture can contain the acids in the free form, in the form of neutral salts or in the form of acid salts. Mixtures which contain free acids and salts can also be used. If all or some of the naphthylaminetrisulphonic acids are present as salts, the alkali metal salts and alkaline earth metal salts, especially the sodium and potassium salts, are preferred. Naphthylaminetrisulphonic acid mixtures which contain the acids in the form of trisodium salts are very particularly preferred.

In addition to the naphthylaminetrisulphonic acids or salts thereof, the naphthylaminetrisulphonic acid mixture can contain other products. Such products can be, in particular, by-products, decomposition products or unreacted intermediate products from the preparation stages for naphthylaminetrisulphonic acids, for example naphthalene-di-, -tri- and -tetra-sulphonic acids, nitronaphthalene-mono-, -di- and -tri-sulphonic acids, and naphthylamine-mono- and -di-sulphonic acids, for example 1-naphthylamine-4,6- and -4,8-disulphonic acid and 2-naphthylamine-4,8-disulphonic acid, and furthermore dinaphthylsulphone-sulphonic acids and amino and nitro derivatives thereof, as well as oxidation products of naphthalene and/or of naphthalenesulphonic acids which can be formed during sulphonation and/or nitration.

The naphthylaminetrisulphonic acid mixture can be employed in the solid form or as an aqueous solution or suspension containing, for example, 20 to 50% by weight, preferably 25 to 40% by weight, calculated as free acid with a molecular weight of 383.

Possible alkali metal hydroxide solutions for the process according to the invention are, in particular, aqueous potassium hydroxide solution or aqueous sodium hydroxide solution. Sodium hydroxide solution is preferably used. 3.5 to 12 mols, for example, of alkali metal hydroxide can be employed per mol of diazotisable substance (calculated with a molecular weight of 383=melanic acid). It is particularly preferable to use 5 to 8 mols of alkali metal hydroxide per mol of diazotisable substance. The concentration of alkali metal hydroxide in the reaction mixture can be, for example, 10 to 50% by weight (relative to the sum of alkali metal hydroxide+total water). This concentration is preferably 20 to 40% by weight.

The reaction can be carried out in a closed vessel at temperatures of 150° to 250° C., preferably at 160° to 220° C. The pressure thereby established is generally completely adequate for carrying out the process according to the invention satisfactorily. The process according to the invention can, of course, also be carried out under pressures other than the autogenous pressures in the closed vessel. Pressures in the range from 5 to 50 bars, for example, are possible for the process according to the invention.

The reaction time essentially depends on the reaction temperature and the alkali metal hydroxide concentration. It is shorter at relatively high reaction temperatures and at relatively high alkali metal hydroxide concentrations and longer at relatively low reaction temperatures and relatively low alkali metal hydroxide concentrations, and is generally 10 minutes to 25 hours. For example, good results are obtained in a reaction time of 90 minutes at a reaction temperature of about 200° C. and at an alkali metal hydroxide concentration of 30% by weight, whilst about 17 hours are required at a reaction temperature of about 170° C.

In carrying out the process according to the invention, it is essential that the alkali metal hydroxide concentrations are favourable during the entire reaction. The process is thus preferably carried out by a procedure in which the naphthylaminetrisulphonic acid isomer mixture, in the form of a weakly alkaline, aqueous solution, and most of the alkali metal hydroxide solution are simultaneously pumped into an initial charge of little alkali metal hydroxide solution in the course of, for example, 5 to 30 minutes, preferably 10 to 20 minutes, and the reaction is then allowed to go to completion.

The starting substances are most appropriately introduced into the reaction vessel at a temperature such that, after the heat of mixing and if appropriate the heat of neutralisation have been released, the desired reaction temperature prevails. It is also possible to bring the starting substances together at lower temperatures and to heat them to the desired reaction temperature in the reaction vessel.

When the reaction has ended and before 1-amino-8-naphthol-3,6-disulphonic acid (H-acid) and 1-amino-8-naphthol-4,6-disulphonic acid (K-acid) have been separated out, it is advantageous to cool the reaction mixture and/or to dilute it with water. It can be cooled, for example, to temperatures in the range from 20° to 150° C., preferably to temperatures the range from 80° to 120° C. The amount of water which may need to be added depends on the reaction conditions, for example the nature of the alkali metal hydroxide and its amount and concentration. It is advantageous to choose the amount of water so that the alkali metal sulphite formed during the reaction is dissolved.

H-Acid and K-acid can be separated out as monoalkali metal salts by acidifying the reaction mixture with mineral acids. Sulphuric acid is preferably used for this. Mineral acid is added in an amount such that the sparingly soluble mono-alkali metal salts of H-acid and K-acid are formed. Appropriate choice of the concentration of mineral acid and/or the addition of water before and/or during the addition of the mineral acid suitably ensures that the inorganic salt formed, for example sodium sulphate or potassium sulphate, does not precipitate. Good results can be obtained, for example, if, to separate out H-acid and K-acid as mono-alkali metal salts, a pH value in the range from 0 to 4, preferably 0.5 to 2.5, is established and 0.1 to 5 times, preferably 0.5 to 2 times, the amount of water, relative to the weight of the mixture present in the hydrolysis under pressure, is introduced by dilution with water and/or by appropriate choice of the concentration of the mineral acid.

The mono-alkali metal salts of H-acid and K-acid can be isolated in various ways. Two preferred variants are given in detail in the following text:

VARIANT 1

The acidified reaction mixture is stirred at temperatures in the range from 40° to 100° C., preferably at 50° to 90° C. and in particular at 60° to 80° C., for some time, for example 1 to 4 hours. The mono-alkali metal salt of H-acid separates out during stirring and can be separated off in the customary manner, for example by filtration. The product separated off is washed with aqueous alkali metal sulphate solution and/or with water and dried, for example in vacuo. The wash liquors are recycled to the following batch in place of water. The filtrate obtained in separating out H-acid is stirred at temperatures in the range from −5° to 40° C., preferably at 5° to 25° C., for some time, for example 2 to 24 hours. The mono-alkali metal salt of K-acid separates out during stirring and can be separated off in the customary manner, for example by filtration. The product separated off is washed with aqueous alkali metal sulphate solution and/or with water and dried, for example in vacuo. The wash liquors are recycled to the following batch in place of water.

VARIANT 2

The acidified reaction mixture is stirred at temperatures in the range from −5° to 40° C., preferably at 5° to 25° C., for some time, for example 2 to 24 hours. A mixture of the mono-alkali metal salts of H-acid and K-acid separates out during stirring and can be separated off in the customary manner, for example by filtration. The product separated off is washed with aqueous alkali metal sulphate solution and the wash liquor is recycled to the following batch in place of water. The H-acid/K-acid mixture separated off is suspended in water and/or aqueous alkali metal sulphate solution, small amounts of mineral acids, preferably sulphuric acid, being added if appropriate, the mono-alkali metal salt of K-acid is dissolved at temperatures in the range from 40° to 100° C., preferably 50° to 90° C. and in particular 60° to 80° C., in the course of some time, for example 1 to 10 hours, and the mono-alkali metal salt of H-acid is obtained by filtering the mixture and washing the residue with aqueous alkali metal sulphate solution and if appropriate water and drying it, for example in vacuo. The wash liquor is recycled to the following batch, in place of water, to prepare the suspension of the H-acid/K-acid mixture. The filtrate which remains after separating off H-acid is stirred at temperatures in the range from −5° to 40° C., preferably 5° to 25° C., for some time, for example 2 to 24 hours, and the mono-alkali metal salt of K-acid is obtained by filtering the mixture and washing the residue with aqueous alkali metal sulphate solution and/or water and drying it, for example in vacuo. The wash liquor is recycled to the following batch, in place of water, for the suspension of the H-acid/K-acid mixture.

In order to remove sulphur dioxide completely, it is advantageous to keep the acidified and dilute mixture at 80° to 100° C. for some time, for example 0.5 to 2 hours, or to blow out the sulphur dioxide with an inert gas, for example nitrogen, after establishing the precipitation conditions and before separating off the mono-alkali metal salts of H-acid and K-acid.

The mono-alkali metal salts of H-acid and K-acid formed can be isolated in high yields and high purities (for example 97–99%, relative to all the organic compounds present) by the process according to the invention.

This is very surprising since a large number of various components can be detected in the mixture present after the hydrolysis under pressure and only about 30 to 40% of the naphthalene employed is present in the form of H-acid and K-acid. In particular, sparingly soluble iso-K-acid (1-amino-6-naphthol-4,8-disulphonic acid) is found, for example, in considerably smaller amounts in the K-acid monoalkali metal salt isolated than when pure melanic acid or the pure di-sodium salt of melanic acid is used (see Example 5).

The process according to the invention offers considerable advantages compared with the hitherto customary alkaline hydrolysis under pressure of melanic acid which has been separated out, and is thus particularly economical. Thus, the process stages for separating out, isolating and redissolving and crystallising T-acid as the acid calcium salt and melanic acid as the acid disodium salt are dispensed with in the process according to the invention. All the T-acid and melanic acid are utilised for the alkaline hydrolysis under pressure, so that an improved yield of H-acid and K-acid, relative to the naphthalene originally employed, results.

The alkaline hydrolysis under pressure can be carried out at higher concentrations when the salt-free melanic acid isomer mixture solution is used than when the disodium salt of melanic acid containing sodium chloride and hydrochloric acid is used. This results in a saving of alkali metal hydroxide at the same concentration of alkali in the reaction mixture. Finally, an effluent is obtained only once in the process according to the invention, namely whilst separating out H-acid and K-acid. In addition to organic compounds, this effluent contains only the inorganic salt formed during the neutralisation, for example sodium sulphate, and a little mineral acid, for example sulphuric acid. Overall, the amounts of effluent and salt are very greatly reduced compared with processes used hitherto.

EXAMPLE 1

689 g of a naphthylaminetrisulphonic acid mixture in the form of trisodium salts (content: 10.02 g of nitrite in total/100 g, 28.6% by weight of melanic acid of MW 383; a total of 69 g of nitrite and 0.51 mol of melanic acid) which has the following composition: 51.4% of 1-naphthylamine-4,6,8-trisulphonic acid, 31.8% of 1-naphthylamine-3,6,8-trisulphonic acid, 9.0% of 2-naphthylamine-4,6,8-trisulphonic acid, 1.2% of 1-naphthylamine-2,5,7-trisulphonic acid, 2.5% of 1-naphthylamine-3,5,7-trisulphonic acid and 0.2% of 2-naphthylamine-3,6,8-trisulphonic acid (the % contents in each case relate to diazotisable substance) and additionally contains 0.6% by weight of the disodium salt of 2-naphthylamine-4,8-disulphonic acid, 0.1% by weight of the disodium salt of 1-naphthylamine-4,8-disulphonic acid, 3.1% by weight of water, 1.4% by weight of sodium carbonate and amounts of amino derivatives and nitro derivatives of dinaphthylsulphone-sulphonic acids and of oxidation products of naphthalene and of naphthalenetrisulphonic acids which cannot be determined quantitatively, and 435 g of water are initially introduced into a 2.7 l nickel autoclave and the mixture is heated to 190° C. 343 g of 70% strength by weight sodium hydroxide solution (6.0 mols of NaOH) are heated to 180° C. in a 1.3 l steel autoclave and are forced into the 2.7 l autoclave with nitrogen, whereupon a 30% strength by weight sodium hydroxide solution forms, relative to the total water. A temperature of 200° C. is established during this procedure. The reaction mixture is kept at 200° C. for 90 minutes and then cooled to 100° C. as rapidly as possible and diluted with 1,800 g of water. The hot reaction solution is acidified with about 1,100 g of 50% strength by weight sulphuric acid whilst controlling the pH (pH 1 to 1.5), is kept at 80° C. for 1 hour whilst nitrogen is passed in for the purpose of removing all of the sulphur dioxide, is cooled to room temperature under evaporative cooling and is kept at room temperature (20° C.) for 12 hours. The product is filtered off at room temperature, washed with a total of 600 g of a 15% strength by weight aqueous sodium sulphate solution and dried at 60° C. in vacuo.

The yield determined by diazotisation is 55%, relative to the nitrite content of the naphthylamine-trisulphonic acid mixture employed. The composition of the mixture of monosodium salts of H-acid/K-acid is determined by high pressure liquid chromatography as follows: 32.1% by weight of the monosodium salt of K-acid, 18.7% by weight of the monosodium salt of H-acid, 0.1% by weight of the monosodium salt of iso-K-acid, φ of the monosodium salt of W-acid, 0.1% by weight of the disodium salt of melanic acid, 0.1% by weight of the disodium salt of T-acid, φ of the disodium salt of dihydroxy-K-acid, 0.4% by weight of the disodium salt of chromotropic acid, 9.2% by weight of water and 39.0% by weight of sodium sulphate. The product isolated does not contain reaction products of the other naphthylamine-di- and -tri-sulphonic acids and of the other by-products.

150 g of the mixture of monosodium salts of K-acid/H-acid are suspended in 350 ml of water. The pH value is adjusted to 1 to 1.5 by adding sulphuric acid and the reaction mixture is stirred at 70° C. for 2 hours. The monosodium salt of H-acid is filtered off at 70° C., washed with a total of 50 ml of a 15% strength aqueous sodium sulphate solution and dried at 60° C. in vacuo. On recycling the wash water, the yield is 62%, relative to T-acid. The H-acid quality is determined by high pressure liquid chromatography as follows: 34.7% by weight of the monosodium salt of H-acid, 1.2% by weight of the monosodium salt of K-acid, $\phi$ of the monosodium salt of W-acid, 0.1% by weight of the monosodium salt of iso-K-acid, 0.2% by weight of the disodium salt of chromotropic acid, 12.4% by weight of water and 51.2% by weight of sodium sulphate.

The monosodium salt of H-acid is obtained in a virtually pure form by renewed suspension of the product in cold water (about 20° C.): 88.1% by weight of the monosodium salt of H-acid, 0.2% by weight of the monosodium salt of K-acid, 9.4% by weight of water and 2.0% by weight of sodium sulphate.

The filtrate obtained from separating off the monosodium salt of H-acid is stirred until it had cooled to room temperature (about 20° C.) and is kept at room temperature for 12 hours. The monosodium salt of K-acid is filtered off, washed with a total of 50 ml of ice-water and dried at 60° C. in vacuo. On recycling the filtrate, the yield is 70%, relative to melanic acid. The K-acid quality is determined by high pressure liquid chromatography as follows: 80.2% by weight of the monosodium salt of K-acid, 2.5% by weight of the monosodium salt of H-acid, $\phi$ of the monosodium salt of iso-K-acid, $\phi$ of the monosodium salt of W-acid, $\phi$ or the monosodium salt of dihydroxy-K-acid, 0.1% by weight of the disodium salt of chromotropic acid, 0.1% by weight of the disodium salt of melanic acid, 0.1% by weight of the disodium salt of T-acid, 12.4% by weight of water and 4.3% by weight of sodium sulphate.

The monosodium salt of K-acid is obtained in virtually pure form by renewed dissolving and crystallising.

EXAMPLE 2

The procedure followed is as in Example 1, but after removing the sulphur dioxide, the reaction mixture is kept at 70° C. for 4 hours. The monosodium salt of H-acid is filtered off at 70° C., washed with a total of 100 ml of a 15% strength by weight aqueous sodium sulphate solution and dried at 60° C. in vacuo. On recycling the wash water to the next batch in place of water, the yield is 61%, relative to T-acid. The H-acid quality corresponds to that of Example 1.

The filtrate is stirred until it had cooled to room temperature (about 20° C.) and is kept at room temperature for 12 hours. The monosodium salt of K-acid is filtered off, washed with a total of 100 ml of ice-water and dried at 60° C. in vacuo. On recycling the wash water to the next batch in place of water, the yield is 70%, relative to melanic acid. The K-acid quality corresponds to that of Example 1.

EXAMPLES 3a TO 3d

The procedure followed is as in Example 1, but the following reaction parameters are varied:
1. Molar ratio of sodium hydroxide solution:melanic acid/T-acid isomer mixture in the form of the trisodium salts
2. Sodium hydroxide solution concentration, relative to the total water
3. Temperature
4. Reaction time The results are summarised in Table 1.

TABLE 1

| | Reaction Conditions | | | | Yield | | | Quality (content)+ | |
|---|---|---|---|---|---|---|---|---|---|
| Example No. | Molar ratio of NaOH to melanic acid/T-acid isomer mixture (MW 383) | NaOH concentration, relative to water % by weight | Temperature °C. | Time hours | K—acid/H—acid (determined by diazotisation) relative to melanic acid/T-acid isomer mixture mol % | K—acid (determined by high pressure liquid chromatography) relative to melanic acid mol % | H—acid (determined by high pressure liquid chromatography) relative to T-acid mol % | K— acid MW 319 % | H— acid MW 319 % |
| 3a | 6:1 | 30 | 170 | 18 | 56 | 71 | 62 | 72.4 | 30.1 |
| 3b | 7.5:1 | 25 | 190 | 4 | 54 | 70 | 60 | 75.0 | 32.0 |
| 3c | 5:1 | 35 | 180 | 8 | 53 | 68 | 61 | 74.5 | 32.5 |
| 3d | 6.5:1 | 30 | 210 | 1 | 54 | 70 | 60 | 73.5 | 29.9 |

+The contents of the organic acids indicated are calculated for the free acid. In fact, these acids are present in the form of the salts indicated in Example 1. The content of by-products in the H—acid and K—acid isolated corresponds to the value in Example 1. Virtually only water and sodium sulphate are still present to make up to 100%.

EXAMPLE 4

733 g of a melanic acid/T-acid isomer mixture in the form of the tripotassium salts (content: 9.41 g of nitrite/100 g, 26.9% by weight of melanic acid of MW 383; a total of 69 g of nitrite and 0.51 mol of melanic acid) which has the following composition: 51.4% of 1-naphthylamine-4,6,8-trisulphonic acid, 30.8% of 1-naphthylamine-3,6,8-trisulphonic acid, 8.2% of 2-naphthylamine-4,6,8-trisulphonic acid, 1.2% of 1-naphthylamine-2,5,7-trisulphonic acid, 2.5% of 1-naphthylamine-3,5,7-trisulphonic acid and 0.2% of 2-naphthylamine-3,6,8-trisulphonic acid (the % contents in each case relate to diazotisable substance) and additionally contains 0.5% by weight of the disodium salt of 2-naphthylamine-4,8-disulphonic acid, 0.1% by weight of the disodium salt of 1-naphthylamine-4,8-disulphonic acid and 3.0% by weight of water and amounts of amino and nitro derivatives of dinaphthylsulphone-sulphonic acids and of oxidation products of naphthalene and of naphthalenetrisulphonic acids which cannot be determined quantitatively, and 780 g of water are heated to 180° C. in a 2.7 l nickel autoclave. 600 g of 70% strength by weight potassium hydroxide solution (7.5 mols of KOH) at 170° C. are forced in with nitrogen. A temperature of 190° C. is established during this procedure, and a 30% strength by weight KOH solution results, relative to the total water.

The reaction mixture is kept at 190° C. for 180 minutes and is cooled to 150° C. in the course of about 2 minutes by means of cooling coils, and after further cooling, is run into 4,500 g of hot water simultaneously with about 1,400 g of 50% strength by weight H₂SO₄, whilst controlling the pH at pH 1 to 1.5 and at 80° to 90° C. The reaction mixture is stirred at 80° to 90° C. for 2 hours to remove sulphur dioxide and is cooled to 20° C. under evaporative cooling and kept at 20° C. for 12 hours. The product is filtered off and washed with a total of 600 g of an approximately 10% strength by weight aqueous potassium sulphate solution.

The yield determined by diazotisation is 50%, relative to the nitrite content of the melanic acid/T-acid isomer mixture employed. The composition of the mixture of the monopotassium salt of K-acid/H-acid is determined by high pressure liquid chromatography as follows: 33.6% by weight of the monopotassium salt of K-acid, 30.7% by weight of the monopotassium salt of H-acid, 0.1% by weight of the monopotassium salt of iso-K-acid, $\phi$ of the monopotassium salt of W-acid, $\phi$ of the dipotassium salt of melanic acid, $\phi$ of the dipotassium salt of T-acid, $\phi$ of the dipotassium salt of dihydroxy-K-acid, 0.6% by weight of the dipotassium salt of chromotropic acid, 2.0% by weight of water and 33.2% by weight of calcium sulphate.

EXAMPLE 5

(Comparison Example)

A reaction carried out as in Example 1 but using the pure trisodium salt of melanic acid gives a yield of K-acid of 74%, but a considerably higher content of iso-K-acid.

Contents in the isolated product: 66.4% of the monosodium salt of K-acid, 6.5% of the monosodium salt of iso-K-acid, 0.2% of the monosodium salt of dihydroxy-K-acid, 0.1% of the monosodium salt of melanic acid, 10.2% of water and 16.8% of sodium sulphate.

What is claimed is:

1. Process for the preparation of mono-alkali metal salts of 1-amino-8-naphthol-4,6-disulphonic acid, which comprises reacting a mixture of naphthylaminetrisulphonic acids and/or salts thereof containing over 40% by weight of 1-naphthylamine-4,6,8-trisulphonic acid relative to the amount of diazotizable substances with an alkali metal hydroxide solution under elevated pressure and at elevated temperature and isolating 1-amino-8-naphthol-3,6-disulphonic aacid (H-acid) and 1-amino-8-naphthol-4,6-disulphonic acid (K-acid), in each case in the form of their mono-alkali metal salts, from the hydrolysis mixture by adjusting its ph-value to a value in the range from 0 to 4 with a mineral acid and by diluting it by introducing 0.1 to 5 times the hydrolysis under pressure and separating off first the H-acid at a temperature in the range from 40° to 100° C. and then the K-acid at a temperature in the range from −5° to 40° C.

2. Process according to claim 1, wherein the isolation of the mono-alkali metal salt of 1-amino-8-naphthol-3,6-di-sulphonic acid (H-acid) is carried out at temperatures in the range from 50° to 90° C.

* * * * *